(12) United States Patent
Powell et al.

(10) Patent No.: US 9,233,077 B2
(45) Date of Patent: *Jan. 12, 2016

(54) DELAYED RELEASE CYSTEAMINE BEAD FORMULATION, AND METHODS OF MAKING AND USING SAME

(71) Applicant: RAPTOR PHARMACEUTICALS INC., Novato, CA (US)

(72) Inventors: Kathlene Powell, Cary, NC (US); Ramesh Muttavarapu, Durham, NC (US)

(73) Assignee: RAPTOR PHARMACEUTICALS INC., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/306,303

(22) Filed: Jun. 17, 2014

(65) Prior Publication Data

US 2014/0370085 A1 Dec. 18, 2014

Related U.S. Application Data

(60) Provisional application No. 61/835,965, filed on Jun. 17, 2013.

(51) Int. Cl.
| | |
|---|---|
| *A61K 31/145* | (2006.01) |
| *A61K 9/48* | (2006.01) |
| *A61K 9/50* | (2006.01) |
| *A61K 31/205* | (2006.01) |

(52) U.S. Cl.
CPC .................. *A61K 9/50* (2013.01); *A61K 9/5026* (2013.01); *A61K 31/145* (2013.01); *A61K 31/205* (2013.01); *A61K 9/5084* (2013.01)

(58) Field of Classification Search
CPC .. A61K 9/5026; A61K 31/145; A61K 9/5084
See application file for complete search history.

(56) References Cited

U.S. PATENT DOCUMENTS

| | | | |
|---|---|---|---|
| 2,809,918 | A | 10/1957 | Hermelin |
| 3,835,221 | A | 9/1974 | Fulberth et al. |
| 4,432,966 | A | 2/1984 | Zeitoun et al. |
| 4,728,512 | A | 3/1988 | Mehta et al. |
| 4,794,001 | A | 12/1988 | Mehta et al. |
| 5,225,202 | A | 7/1993 | Hodges et al. |
| 8,129,433 | B2 | 3/2012 | Dohil et al. |
| 2001/0005716 | A1 | 6/2001 | Ullah et al. |
| 2009/0076166 | A1 | 3/2009 | Dohil et al. |

OTHER PUBLICATIONS

Owen, B. et al., Development of Cysteamine Hydrochloride Pellets for Cystinotic Infants, European Hospital Pharmacy, 3(4): 136-142 (1997).
Owen, B. et al., Film Coating of Cysteamine Hydrochloride Pellets for the Treatment of Cystinosis in Children, Pharmaceutical Technology Conference, 20:139-140 (2001).
Owen, B. et al., Pilot Scale Manufacture of Gastro-Resistant Cysteamine Hydrocholoride Pellets Using Extrusion Spherization and Fluid Bed Coating, 15th Pharmaceutical Technology Conference, 1:116-119 (1996).
Owen, B. et al., The Effect of Colloidal Grade of Microcrystalline Cellulose on the Extrusion Rheology and Spheronisation of Cysteamine Hydrochloride Formulations, 16th Pharmaceutical Technology Conference, pp. 1-8 (1997).
Owen, Berwyn, Formulation and Processing of Cysteamine Hydrochloride Gastro-Resistant Pellets for the Treatment of Cystinosis, A thesis submitted to Institute of Pharmacy and Chemistry School of Sciences, University of Sunderland, pp. 1-256 (2000).
Wen, H. et al., Limiting Factors for Oral CR Formulations, in Oral Controlled Release Formulation Design and Drug Delivery: Theory to Practice, John Wiley & Sons, Inc., p. 3 (2010).
Zhou, D. et al., Understanding Biopharmaceutics Properties for Pharmaceutical Product Development and Manufacturing I-Oral Absorption and the Biopharmaceutics Classification System, Journal of Validation Technology, pp. 62-72 (2009).
Belldina et al., "Steady-State Pharmacokinetics and Pharmacodynamics of Cysteamine Bitartrate in Paediatric Nephropathic Cystinosis Patients," Br. J. Clin. Pharmacol., 56(5):520-525 (Published online Aug. 4, 2003).
Gangoiti et al., "Pharmacokinetics of Enteric-Coated Cysteamine Bitartrate in Healthy Adults: A Pilot Study," Br. J. Clin. Pharmacol., 70(3):376-382 (Published online Jun. 8, 2010).
Clinical Pharmacology and Biopharmaceutics Review(s), Center for Drug Evaluation and Research, Application No. 203389Orig1s000, compilation from http://www.accessdata.fda.gov/drugsatfda_docs/nda/2013/203389Orig1s000ClinPharmR.pdf , consisting of numbered pp. 1-28, numbered pp. 1-12, and electronic signature page (Reference ID: 3287734); numbered p 1-10 with electronic signature page (Reference ID: 3261783) and numbered pp. 1-4 with signature page (Reference ID: 3129161) (Available no earlier than Apr. 30, 2013).
Langman, C. B. et al., A Randomized Controlled Crossover Trail with Delayed-Release Cysteamine Bitartrate in Nephropathic Cystinosis: Effectiveness on White Blood Cell Cystine Levels and Comparison of Safetly, Clinical Journal of Society of Nephrology, 7(7):1112-1120 (Published online May 2012).
Langman, C. B. et al., Quality of Life is Improved and Kidney Function Preserved in Patients with Nephropathic Cystinosis Treated for 2 years with Delayed-Release Cysteamine Bitartrate, Journal of Pediatrics, 165(3)528-533 (Published online Jun. 2014).
Raptor Pharmaceuticals Inc., Procysbi (cysteamine bitartrate) delayed-release capsules, Highlights of Prescribing Information, pp. 1-13 (Available no earlier than Apr. 30, 2013).
Dohil et al., "The Effect of Food on Cysteamine Bitartrate Absorption in Healthy Participants," Clin, Pharmacol. Drug Dev. 1(4) 170-174 (Oct. 2012).
Dohil et al., "Twice-Daily Cysteamine Bitartrate Therapy for Children with Cystinosis," J. Pediatr., 156(1) p. 71-75 (Published online Sep. 23, 2009).

(Continued)

*Primary Examiner* — Anoop Singh
*Assistant Examiner* — Doan Phan
(74) *Attorney, Agent, or Firm* — Marshall, Gerstein & Borun LLP

(57) ABSTRACT

An enteric-coated bead dosage form of cysteamine, and related methods of manufacture and use, are disclosed.

23 Claims, No Drawings

(56) References Cited

OTHER PUBLICATIONS

Dohil et al., "Long-Term Treatment of Cystinosis in Children with Twice-Daily Cysteamine," J. Pediatr. 156(5), p. 823-27 (Published online Feb. 8, 2010).

Fidler et al., "Pharmacokinetics of Cysteamine Bitartrate following gastrointestinal infusion," Br. J. Clin. Pharmacol. 63(1) p. 36-40 (Published online Aug. 16, 2006).

Tenneze et al., A study of the relative bioavailability of cysteamine hydrochloride cysteamine bitartrate and phosphocysteamine in healthy adult male volunteers, Br. J. Clin. Pharmacol, 47(1):49-52 (1999).

Scheider et al., Recent advances in the treatment of cystinosis, J. Inher. Metab. Dis., 18(4):387-97 (1995).

Goodhart et al., "An Evaluation of Aqueous Film-Forming Dispersions for Controlled Release," Pharm. Tech., 8(4):64-71 (1984).

IBIE, Co., "Development and Evaluation of Oral Solid Dosage Forms for Colonic Delivery of Drugs for the Treatment of Cystinosis," Robert Gordon University, Thesis (2010).

Remington's Pharmaceutical Sciences, A. Osol, ed., Mack Pub. Co., 16th ed., pp. 1590-1593 (1980).

International Search Report and Written Opinion for Application No. PCT/US2014/042607, dated Oct. 2, 2014.

DELAYED RELEASE CYSTEAMINE BEAD FORMULATION, AND METHODS OF MAKING AND USING SAME

CROSS-REFERENCE TO RELATED APPLICATION

The benefit under 35 U.S.C. §119(e) of U.S. Provisional Patent Application Ser. No. 61/835,965 filed Jun. 17, 2013, is hereby claimed, and the disclosure thereof is hereby incorporated by reference herein.

BACKGROUND

1. Field of the Disclosure

The disclosure relates generally to delayed release formulations of cysteamine and pharmaceutically acceptable salts thereof, and related methods of making and treatment, e.g. treatment of cystinosis and other metabolic and neurodegenerative diseases including non-alcoholic fatty liver disease (NAFLD), Huntingon's disease, Parkinson's disease, Rett Syndrome and others, use as free radical and radioprotectants, and as hepto-protectant agents. More particularly, the disclosure relates to enteric coated beads comprising cysteamine or a pharmaceutically acceptable salt thereof.

2. Brief Description of Related Technology

Cystinosis is a rare, autosomal recessive disease caused by intra-lysosomal accumulation of the amino acid cystine within various tissues, including the spleen, liver, lymph nodes, kidney, bone marrow, and eyes. Nephropathic cystinosis is associated with kidney failure that necessitates kidney transplantation. A specific treatment for nephropathic cystinosis is the sulfhydryl agent, cysteamine. Cysteamine has been shown to lower intracellular cystine levels, thereby reducing the rate of progression of kidney failure in children.

An enterically-coated cysteamine composition has been described, for increasing delivering of cysteamine to the small intestine and resulting in less frequent dosing compared to non enteric-coated cysteamine.

SUMMARY

One aspect of the disclosure provides a pharmaceutical dosage form including a plurality of cysteamine beads, the beads including a core particle including cysteamine or a pharmaceutically acceptable salt thereof and a pharmaceutically acceptable excipient, and an enteric membrane surrounding the core, wherein the plurality of beads is characterized by a distribution of particle sizes.

Another aspect of the disclosure provides a pharmaceutical dosage form including a plurality of cysteamine beads, the beads including a core particle including cysteamine or a pharmaceutically acceptable salt thereof and a pharmaceutically acceptable excipient, and an enteric membrane surrounding the core, wherein the plurality of beads is characterized by irregular bead shapes.

Yet another aspect of the disclosure provides a pharmaceutical dosage form including a plurality of cysteamine beads, the beads including a core particle including cysteamine or a pharmaceutically acceptable salt thereof and a pharmaceutically acceptable excipient, and an enteric membrane surrounding the core, wherein the plurality of beads is characterized by a distribution of enteric membrane thicknesses.

Still another aspect of the disclosure provides a method of making a pharmaceutical dosage form, including any embodiment described herein, by a method including coating a core particle including cysteamine or a pharmaceutically acceptable salt thereof and an excipient with an enteric polymer to form an enteric membrane. The method can include sorting core particles prior to enteric coating, to provide a selected core particle size distribution. The method can also include sorting enteric coated beads to provide a selected bead size distribution.

Yet another aspect of the disclosure provides a method for treating a patient in need of cysteamine comprising administering to the patient a dosage form described herein, including any embodiment described herein.

Still another aspect of the disclosure provides dosage forms and related methods according the disclosure herein wherein the primary active component is cystamine rather than cysteamine or a pharmaceutically acceptable salt thereof.

For the compositions and methods described herein, optional features, including but not limited to components, compositional ranges thereof, substituents, conditions, and steps, are contemplated to be selected from the various aspects, embodiments, and examples provided herein.

Further aspects and advantages will be apparent to those of ordinary skill in the art from a review of the following detailed description. While the dosage form, method of making, and method of treatment are susceptible of embodiments in various forms, the description hereafter includes specific embodiments with the understanding that the disclosure is illustrative, and is not intended to limit the invention to the specific embodiments described herein.

DETAILED DESCRIPTION

Described herein is pharmaceutical dosage form that includes a plurality of cysteamine beads, the beads including a core particle including cysteamine or a pharmaceutically acceptable salt thereof and a pharmaceutically acceptable excipient, and an enteric membrane surrounding the core particle. The plurality of beads can be characterized by a distribution of particle sizes. The plurality of beads can be characterized by irregular bead shapes. The plurality of beads can be characterized by a distribution of enteric membrane thicknesses. Also disclosed herein are a method for the preparation of the dosage form, including coating a core particle including cysteamine or a pharmaceutically acceptable salt thereof and an excipient with an enteric polymer to form the enteric membrane. Optionally, the core particle can be formed by a wet granulation method. Optionally, granules are sorted (e.g., via sieving) to a desired particle size range prior to enteric coating, and optionally again following enteric coating. Also disclosed herein are treatment methods including administering the dosage form to a patient in need thereof.

Cysteamine-containing, enteric-coated beads characterized by a distribution of particle sizes were shown to exhibit advantageous pharmacokinetics. Without intending to be bound by any particular theory, it is contemplated that the pharmacokinetics are influenced by the plurality of enteric-coated beads having a distribution of core particle sizes.

Cysteamine-containing, enteric-coated beads characterized by a irregular bead shapes were shown to exhibit advantageous pharmacokinetics. Without intending to be bound by any particular theory, it is contemplated that the pharmacokinetics are influenced by the plurality of enteric-coated beads having irregular bead shapes.

Cysteamine-containing, enteric-coated beads characterized by a distribution of enteric membrane thicknesses were shown to exhibit advantageous pharmacokinetics. Without intending to be bound by any particular theory, it is contemplated that the pharmacokinetics are influenced by the plurality of enteric-coated beads having a distribution of enteric membrane thicknesses.

In one aspect the distribution of enteric membrane thicknesses can be stated in terms of weight gain of enteric membrane material based on the total weight of the coated beads. Thus, in one embodiment, the distribution of enteric membrane thicknesses will be at least 2% based on the total weight of the coated beads. In another embodiment, the distribution of enteric membrane thicknesses will be at least 3%. In another embodiment, the distribution of enteric membrane thicknesses will be at least 4%. In another embodiment, the distribution of enteric membrane thicknesses will be at least 5%. In another embodiment, the distribution of enteric membrane thicknesses will be at least 6%. In another embodiment, the distribution of enteric membrane thicknesses will be at least 7%. In another embodiment, the distribution of enteric membrane thicknesses will be at least 8%. In another embodiment, the distribution of enteric membrane thicknesses will be at least 9%. In another embodiment, the distribution of enteric membrane thicknesses will be at least 10%. In another embodiment, the distribution of enteric membrane thicknesses will be at least 11%. In another embodiment, the distribution of enteric membrane thicknesses will be at least 12%. In another embodiment, the distribution of enteric membrane thicknesses will be at least 13%. In another embodiment, the distribution of enteric membrane thicknesses will be at least 14%. For example, the difference in enteric membrane thickness from bead to bead can be in a range of +/−1-7% based on the total weight of the coated beads. The distribution of enteric membrane thicknesses can be in a range of about 2% to about 14% based on the weight of the coated beads, or in a range of about 3% to about 13%, or in a range of about 4% to about 12%, or in a range of about 5% to about 11%, or in a range of about 6% to about 10%, or in a range of about 7% to 9%, or in a range of about 3% to 14%, or in a range of about 4% to 14%, or in a range of about 4% to 13%, or in a range of about 4% to about 12%, for example. In one embodiment, the absorption (AUC) of the dosage form when dosed orally is advantageously increased, compared to other dosage forms of cysteamine. Without intending to be bound by any particular theory, it is contemplated that the increase in absorption is influenced by the dosage form exhibiting a pseudo-extended release profile. The pseudo-extended release profile is contemplated to be influenced by one or more factors, including a distribution of enteric membrane thicknesses, a distribution of bead particle sizes, and the beads having irregular bead shapes. For example, in an embodiment wherein the beads have a distribution of enteric membrane thicknesses, it is contemplated that for beads which have a relatively thin coating, the coating will completely dissolve at the trigger pH relatively quickly to release the cysteamine composition, whereas for beads having a relatively thick coating the coating will take somewhat longer to completely dissolve and release the cysteamine composition. In another aspect, in an embodiment where the beads have a distribution of particle sizes and/or irregular bead shapes, it is contemplated that the gut transit time of the beads could be varied due to bead size and/or shape, such that the transit time until reaching the enteric membrane dissolution pH is varied, thus contributing to a pseudo-extended release profile. In another embodiment, the dosage form exhibits substantially equivalent (e.g., bioequivalent) Cmax and/or AUC characteristics when administered orally inside a capsule shell or without a capsule shell.

The dosage form provides a progressive and predictable absorption curve. In one type of embodiment, the Tmax of the dosage form when dosed orally is advantageously more stable on a dose-to-dose basis, because the beads are individually enteric-coated. A predictable, consistent Tmax is highly advantageous for accomplishing a more consistent, sustained reduction of leukocyte cystine levels by use of cysteamine. For example, process-related variations in enteric membrane thickness or other influences on enteric membrane dissolution will affect only a fraction of the cysteamine in the dosage form and will tend to lead to the pseudo-extended release behavior described above. In contrast, enteric-coated capsules comprising cysteamine microspheres exhibited significant variability in absorption time from capsule to capsule.

In another embodiment, the dosage form exhibits advantageous storage stability, e.g. as measured by the amount of cystamine present following storage and/or by the total amount of related substances. The storage stability can be assessed following storage at typical ambient conditions (e.g. 25° C. and 40% relative humidity) or at accelerated stability conditions involving increased temperature and/or humidity.

The dosage form and methods are contemplated to include embodiments including any combination of one or more of the additional optional elements, features, and steps further described below (including those shown in the figures and Examples), unless stated otherwise.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "comprising" indicates the potential inclusion of other agents, elements, steps, or features, in addition to those specified.

As used herein, the term wt. % is the weight percent based on the total weight, e.g. of the core particle, or enteric membrane, or total bead, as described in context. Unless stated otherwise, the wt. % is intended to describe the weight percent based on dry weight (e.g., for a core particle following drying).

All ranges set forth herein include all possible subsets of ranges and any combinations of such subset ranges. By default, ranges are inclusive of the stated endpoints, unless stated otherwise Where a range of values is provided, it is understood that each intervening value between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also contemplated to be part of the disclosure.

Unless expressly stated otherwise, all references to cysteamine herein are intended to encompass pharmaceutically-acceptable salts thereof, and for every reference to cysteamine herein the use of cysteamine bitartrate is specifically contemplated as an embodiment. As described in the Summary above, embodiments of the dosage forms and methods described herein can employ cystamine as the primary active component, rather than cysteamine or a pharmaceutically acceptable salt thereof.

Unless expressly stated otherwise, reference herein to a bead and properties thereof is intended to be interpreted as applying equally to a collection of beads (e.g., a plurality of such beads). Likewise, unless expressly stated otherwise, reference herein to a core particle and properties thereof is intended to be interpreted as applying equally to a collection of core particles (e.g., a plurality of such core particles).

As described above, a pharmaceutical dosage form is contemplated that includes a plurality of cysteamine beads, the beads including a core particle including cysteamine or a pharmaceutically acceptable salt thereof and a pharmaceutically acceptable excipient, and an enteric membrane surrounding the core particle, wherein the plurality of beads is characterized by a distribution of particle sizes.

In one embodiment, the particle sizes of the beads are in a range of about 0.7 mm to about 2.5 mm, or about 0.7 mm to about 2.8 mm, or about 0.8 mm to about 1.7 mm. For example, the target bead size can be up to 2.5 mm with no more than 10 percent variation over this size, to a maximum size of 2.8 mm.

As the particle size of the beads becomes too small, the variability in cysteamine content increases. As the particle size becomes too large, the beads are too large for use in drug products that are labeled to be administered via sprinkling (e.g., on applesauce or other soft foods, such as jellies) and swallowed without chewing, or administered via an enteral feeding tube. Also as the particle size increases, it was found that the larger particles get coated more than the smaller particles, resulting in lower relative assay when compared to use of smaller particles. To compensate, relatively more such beads would be needed in order to meet the label strength per capsule, but because salts such as cysteamine bitartrate already have a high molecular weight, filling a capsule shell with sufficient large particles to meet the label strength per capsule becomes difficult or impossible (e.g. to fill a size 0 capsule to a 75 mg strength of cysteamine free base). Accordingly the bead particle size in one type of embodiment is up to 1.7 mm.

The distribution of bead particle sizes for various non-exclusive embodiments of the invention can be characterized in ways.

In one embodiment, the beads can be characterized by 5% or less of the beads by weight being retained on a #12 mesh (1.68 mm) screen and 10% or less by weight passing through a #20 mesh (0.84 mm) screen. In another embodiment, at least 80% by weight of the beads have a particle size in a range of about 850 µm to about 1180 µm, e.g. as determined by sieving.

The distribution of bead sizes can be characterized by a gradation test via analytical sieving. Thus, in another embodiment the distribution of bead sizes is characterized by 0% of the beads being retained on a 1700 µm sieve and less than 5% by weight of the beads being retained on a 1400 µm sieve. Optionally less than 30% by weight of the beads are retained on a 1180 µm sieve. Optionally less than 70% by weight of the beads are retained on a 1000 µm sieve. Optionally less than 20% by weight of the beads are retained on a 850 µm sieve. Optionally at least 15% by weight of the beads are retained on a 1180 µm sieve. Optionally at least 50% by weight of the beads are retained on a 1000 µm sieve. Optionally at least 10% by weight of the beads being retained on a 850 µm sieve.

Thus, for example, the distribution can be characterized by 0% of the beads being retained on a 1700 µm sieve and less than 5% by weight of the beads being retained on a 1400 µm sieve, and about 20% to about 30% by weight of the beads being retained on a 1180 µm sieve and then about 50% to about 70% (or about 55% to about 65%) by weight of the beads being retained on a 1000 µm sieve and then about 10% to about 20% by weight of the beads being retained on a 850 µm sieve.

In another embodiment, the distribution of bead sizes can be characterized by a median particle size in a range of about 850 µm to about 1180 µm.

The bead core particle can comprise one or more excipients. In one type of embodiment, the excipients can include one or more fillers, binders, and surfactants. Other optional ingredients can include, but are not limited to, glidants, lubricants, disintegrants, swelling agents, and antioxidants.

Fillers include, but are not limited to, lactose, saccharose, glucose, starch, microcrystalline cellulose, microfine cellulose, mannitol, sorbitol, calcium hydrogen phosphate, aluminum silicate, amorphous silica, and sodium chloride, starch, and dibasic calcium phosphate dehydrate. In one type of embodiment, the filler is not water soluble, although it may absorb water. In one type of embodiment, the filler is a spheronization aid. Spheronization aids can include one or more of crospovidone, carrageenan, chitosan, pectinic acid, glycerides, β-CD, cellulose derivatives, microcrystalline cellulose, powdered cellulose, polyplasdone crospovidone, and polyethylene oxide. In one embodiment, the filler includes microcrystalline cellulose.

Binders include, but are not limited to, cellulose ethers, methyl cellulose, ethyl cellulose, hydroxyethyl cellulose, propyl cellulose, hydroxypropyl cellulose, lower-substituted hydroxypropyl cellulose, hydroxypropylmethyl cellulose (hypromellose, e.g. hypromellose 2910, METHOCEL E), carboxymethyl cellulose, starch, pregelatinized starch, acacia, tragacanth, gelatine, polyvinyl pyrrolidone (povidone), cross-linked polyvinyl pyrrolidone, sodium alginate, microcrystalline cellulose, and lower-substituted hydroxypropyl cellulose. In one embodiment, the binders are selected from wet binders. In one type of embodiment, the binder is selected from cellulose ethers, e.g. hypromellose.

Surfactants include, but are not limited to, anionic surfactants, including sodium lauryl sulfate, sodium deoxycholate, dioctyl sodium sulfosuccinate, and sodium stearyl fumarate, nonionic surfactants, including polyoxyethylene ethers, and polysorbate 80, and cationic surfactants, including quaternary ammonium compounds. In one embodiment the surfactant is selected from anionic surfactants, e.g. sodium lauryl sulfate.

Disintegrants include, but are not limited to, starch, sodium cross-linked carboxymethyl cellulose, carmellose sodium, carmellose calcium, cross-linked polyvinyl pyrrolidone, and sodium starch glycolate, low-substituted hydroxypropyl cellulose, hydroxypropyl starch.

Glidants include, but are not limited to, polyethylene glycols of various molecular weights, magnesium stearate, calcium stearate, calcium silicate, fumed silicon dioxide, magnesium carbonate, magnesium lauryl sulfate, aluminum stearate, stearic acid, palmitic acid, cetanol, stearol, and talc.

Lubricants include, but are not limited to, stearic acid, magnesium stearate, calcium stearate, aluminum stearate, and siliconized talc.

The amount of cysteamine free base in the core particle can be at least 10 wt. % or at least 15 wt. %, or at least 20 wt. %, or at least 25 wt. %, or at least 30 wt. %. For example, the amount of cysteamine bitartrate can be at least 50 wt. %, or at least 55 wt. %, or at least 60 wt. %, or at least 65 wt. %, or at least 70 wt. %, or at least 75 wt. %, or at least 80 wt. %, or at least 85 wt. % of the core particle, for example in a range of about 60 wt. % to about 90 wt. % or about 65 wt. % to about 85 wt. %. It is understood that any and all ranges including these values as endpoints is contemplated, for example, at least about 15 wt. % to about 90 wt. %, or at least about 20 wt. % to about 85 wt. %, or at least about 30 wt. % to about 85 wt. %, or at least about 50 wt. % to about 90 wt. %. As the dose of cysteamine free base can be up to about 2 g/m$^2$/day, and the amount of free base is relatively small compared to the molecular weight of salts (e.g. the bitartrate salt) it is preferred that the core particle have as much active ingredient as possible while allowing the creation and processing of core particles.

The amount of filler in the core particle is not particularly limited. In embodiments, the amount of filler (e.g. microcrystalline cellulose) can be in a range of about 10 wt. % to about 30 wt. %, or about 16 wt. % to about 23 wt. %, or at least 19 wt. % or at least 19.5 wt. %, for example about 20 wt. %.

The amount of binder in the core particle is not particularly limited. In embodiments, the amount of binder (e.g. hypromellose) can be in a range of about 1 wt. % to about 10 wt. %, or about 2 wt. % to about 8 wt. %, or about 4 wt. % to about 6 wt. %, for example about 5 wt. %.

The amount of surfactant, e.g. as a processing aid, in the core particle is not particularly limited. In embodiments, the amount of surfactant (e.g. microcrystalline cellulose) can be in a range of about 0.1 wt. % to about 1 wt. %, or about 0.2 wt. % to about 0.8 wt. %, or about 0.4 wt. % to about 0.6 wt. %, for example about 0.5 wt. %.

The enteric (gastro-resistant) membrane material, e.g. polymer, can be one that will dissolve in intestinal juices at a pH level higher than that of the stomach, e.g. a pH of greater than 4.5, such as within the small intestine, and therefore permit release of the active substance in the regions of the small intestine and substantially not in the upper portion of the GI tract. In one type of embodiment, the enteric material begins to dissolve in an aqueous solution at pH between about 4.5 to about 5.5. In another type of embodiment, the enteric material rapidly dissolves in an aqueous solution at pH between of about 5. In another type of embodiment, the enteric material rapidly dissolves in an aqueous solution at pH between of about 5.5.

For example, pH-sensitive materials will not undergo significant dissolution until the dosage form has emptied from the stomach. The pH of the small intestine gradually increases from about 4.5 to about 6.5 in the duodenal bulb to about 7.2 in the distal portions of the small intestine (ileum). In order to provide predictable dissolution corresponding to the small intestine transit time of about 3 hours (e.g., 2-3 hours) and permit reproducible release therein, the membrane should begin to dissolve within the pH range of the duodenum, and continue to dissolve at the pH range within the small intestine. Therefore, the amount (thickness) of enteric membrane should be sufficient to be substantially dissolved during the approximate three hour transit time within the small intestine (e.g., the proximal and mid-small intestine).

Enteric (gastro-resistant) materials can include, but are not limited to, one or more of the following: cross-linked polyvinyl pyrrolidone; non-cross linked polyvinylpyrrolidone; hydroxypropylmethyl cellulose phthalate, hydroxypropylmethyl cellulose acetate succinate, cellulose acetate succinate; cellulose acetate phthalate, hydroxypropylmethyl cellulose acetate succinate, cellulose acetate trimellitate; starch acetate phthalate; polyvinyl acetate phthalate; carboxymethyl cellulose; methyl cellulose phthalate; methyl cellulose succinate; methyl cellulose phthalate succinate, methyl cellulose phthalic acid half ester; ethyl cellulose succinate; carboxymethylamide; potassium methacrylatedivinylbenzene copolymer; polyvinylalcohols; polyoxyethyleneglycols; polyethylene glycol; sodium alginate; galactomannone; carboxypolymethylene; sodium carboxymethyl starch; copolymers of acrylic acid and/or methacrylic acid with a monomer selected from the following: methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate, or octadecyl acrylate, e.g. EUDRAGIT-L and -S series, including L 100-55, L 30 D-55, L 100, S 100, L 12.5, and S 12.5, available from Evonik Industries; polyvinyl acetate; fats; oils; waxes; fatty alcohols; shellac; zein; gluten; ethylacrylate-maleic acid anhydride copolymer; maleic acid anhydride-vinyl methyl ether copolymer; styrol-maleic acid copolymer; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; polyarginine; poly(ethylene); poly(propylene); poly(ethylene oxide); poly(ethylene terephthalate); poly(vinyl isobutyl ether); poly(vinyl chloride); and polyurethane. A combination of enteric materials may also be used. In one embodiment, the enteric material rapidly dissolves at pH 5.5 and higher, to provide fast dissolution in the upper bowel. For example, the enteric material can be selected from a copolymer of methacrylic acid and methyl methacrylate, and a copolymer of methacrylic acid and ethyl acrylate. For example, an enteric polymer is poly(methacrylic acid co-ethyl acrylate) 1:1 (EUDRAGIT L 30 D-55 and EUDRAGIT L100-55).

Examples of some enteric coatings are disclosed in U.S. Pat. No. 5,225,202, including beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit L30D) (F. W. Goodhart et al., Pharm. Tech., pp. 64-71, April 1984); copolymers of methacrylic acid and methacrylic acid methylester (Eudragits), or a neutral copolymer of polymethacrylic acid esters containing metallic stearates (Mehta et al., U.S. Pat. Nos. 4,728,512 and 4,794,001). Such coatings comprise mixtures of fats and fatty acids, shellac and shellac derivatives and the cellulose acid phthlates, e.g., those having a free carboxyl content. See also Remington's Pharmaceutical Sciences, A. Osol, ed., Mack Pub. Co., Easton, Pa. (16th ed. 1980) at pages 1590-1593, and Zeitova et al. (U.S. Pat. No. 4,432,966), for descriptions of suitable enteric coating compositions.

One or more plasticizers can be added to enteric polymers in order to increase their pliability and reduce brittleness, as it is known in the art. Suitable plasticizers are known in the art and include, for example, butyl citrates, triethyl citrate, diethyl phthalate, dibutyl sebacate, PEGs (e.g. PEG 6000), acetyl triethyl citrate, and triacetin. In one type of embodiment, the plasticizer is triethyl citrate. While some enteric materials are flexible and do not require addition of plasticizers, more brittle polymers (e.g., Eudragit L/S types, Eudragit RL/RS, and Eudragit FS 30 D) benefit from plasticizers, e.g. in the range of 5 wt. % to 30 wt. % based on the dry polymer mass, e.g. about 8 wt. % to about 12 wt. % triethyl citrate with poly(methacrylic acid co-ethyl acrylate) 1:1.

One or more anti-tacking agents (antiadherents) can also be added to an enteric coating mixture in order to reduce the tackiness of the film and prevent agglomeration, as it is known in the art. Anti-tacking agents include talc, and glyceryl monostearate, fumed silica (e.g., AEROSIL 200), precipitated silica (e.g., SIPERNAT PQ), and magnesium stearate, for example. Anti-tacking agents can be used in any suitable quantity, for example in a range of about 10 wt. % to 100 wt. % based on dry polymer mass, or about 10 wt. % to about 50 wt. %, or about 10 wt. % to about 30 wt. %, or about 15 wt. % to about 30 wt. %. For example, in one embodiment the amount of talc is in a range of 15 wt. % to about 30 wt. %, based on dry polymer mass.

One or more surfactants can also be added to an enteric coating mixture in order to improve substrate wettability and/or stabilize suspensions, as it is known in the art. Surfactants include Polysorbate 80, sorbitan monooleate, and sodium dodecyl sulfate, for example.

The enteric membrane can be formed by any suitable process. Coating processes include pan coating, fluid bed coating, and dry coating (e.g., heat dry coating and electrostatic dry coating), for example. Pan coating and fluid bed coating using solvent are well established processes. In liquid coating, the enteric material and optional excipients (e.g. pigments, plasticizers, anti-tacking agents) are mixed in an organic solvent or water to form a solution or dispersion. The coating solution or dispersion is sprayed into solid dosage forms in a pan coater or a fluid bed dryer and dried by hot air. For example, in a Wurster fluid bed coating process, the coating fluid is sprayed from the bottom of the fluid bed apparatus, whereas in an alternative the coating fluid is applied by top spraying, and in another alternative tangential spray is applied.

The amount of enteric material applied is sufficient to achieve desired acid resistance and release characteristics. For example, in one embodiment the amount of enteric membrane will be sufficient to meet United States Pharmacopeia (USP) <711> requirements (USP 36-NF 31) for delayed-release dosage forms, thereby not releasing 10.0 wt. % of drug after 2 hours in 0.1N HCl. In another aspect, the formulation will be sufficient to release at least 80% of the active in 20 minutes in pH 6.8 buffer solution, e.g. using the dissolution method of USP 36-NF 31 section <711>.

In one type of embodiment, the enteric membrane is present in an amount in a range of about 20% to 40%, or 25% to about 35% as measured by the weight gain compared to the uncoated particle cores, or in a range of about 25% to about 31% weight gain, or about 27% to about 31% weight gain, or about 28.5% to about 31% weight gain, based on the weight of the uncoated particle cores.

The beads with enteric membrane can be sorted (e.g., via sieving) to a desired particle size. In embodiments, the particle size range can be any particle size range or combination thereof described above in connection with the core particles. In one type of embodiment, the particle size range will be the same as the particle size range of the uncoated core particles. For example, the beads can be sieved such that 5% or less of the bead core particles by weight are retained on a #12 mesh (1.68 mm) screen and 10% or less by weight pass through a #20 mesh (0.84 mm) screen.

Additional lubricant (glidant, anti-tack agent) can be added to the coated beads in powder form. Anti-tacking agents include talc, glyceryl monostearate, fumed silica (e.g., AEROSIL 200), and precipitated silica (e.g., SIPERNAT PQ), for example. For example talc powder can be added to the coated beads, for example in an amount of 0.1 wt. % to about 1 wt. % based on the total bead weight.

The formulation can include a capsule shell in which the beads are disposed. Soft and hard capsule shells are known. In one embodiment, the capsule shell is a hard capsule shell, e.g. a gelatin capsule shell or a vegetable-based hard capsule shell.

Thus, for example, one type of embodiment combining various of the features described above includes a pharmaceutical dosage form including a plurality of cysteamine beads, the beads including a core particle comprising cysteamine bitartrate, a filler (optionally microcrystalline cellulose), a binder (optionally hypromellose), and an enteric membrane (optionally Eudragit L30 D-55) surrounding the core, wherein the plurality of beads is characterized by a distribution of particle sizes in a range of about 0.7 mm to about 2.5 mm, wherein the enteric membrane is present in an amount in a range of about 20% to about 40% based on the weight of the bead core particles, and wherein the beads are disposed in a capsule shell.

Pharmacokinetics

As mentioned above, the dosage form can advantageously be designed have one or more pharmacokinetic characteristics, e.g. in humans.

In one embodiment, the pharmaceutical dosage form is characterized by a mean Tmax upon oral dosing, fasted, of greater than 75 minutes, or at least 110 minutes, or at least 2 hours, or at least 3 hours, or in a range of about 2.2 hours to about 3.48 hours, or about 2.22 hours to about 3.34 hours, or about 2.78 hours, or a Tmax in a range of 80% to 125%, or 80% to 120% of such reference Tmax.

In another embodiment, the pharmaceutical dosage form is characterized by a mean Cmax upon oral dosing, fasted, in a range of about 22.16 μmol/L to about 34.63 μmol/L, or about 22.16 μmol/L to about 33.24 μmol/L, or about 22.7 μmol/L, normalized to a 450 mg dose, or a Cmax in a range of 80% to 125%, or 80% to 120% of such reference Cmax. In another embodiment, the pharmaceutical dosage form is characterized by a mean Cmax_D upon oral dosing in a range of about 0.004 to about 0.006 mg/L/mg.

In another embodiment, the pharmaceutical dosage form is characterized by a mean AUC (0-6 hours) upon oral dosing, fasted, in a range of about 60.74 μmol·h/L to about 94.91 μmol·h/L, or about 60.74 μmol·h/L to about 91.12 μmol·h/L, or about 75.93 μmol·h/L, normalized to a 450 mg dose, or a bioequivalent AUC (0-6 hours) in a range of 80% to 125%, or 80% to 120% of such reference AUC (0-6 hours). In another embodiment, the pharmaceutical dosage form is characterized by a mean AUC (0-12 hours) upon oral dosing in a range of about 79.41 μmol·h/L to about 124.08 μmol·h/L, or about 79.41 μmol·h/L to about 119.11 μmol·h/L, or about 99.26 μmol·h/L, normalized to a 450 mg dose, or a bioequivalent AUC (0-12 hours) in a range of 80% to 125%, or 80% to 120% of such reference AUC (0-12 hours). In another embodiment, the pharmaceutical dosage form is characterized by a mean AUC (0-inf_D) upon oral dosing in a range of about 0.86 min·mg/L/mg to about 1.35 min·mg/L/mg, or about 0.86 min·mg/L/mg to about 1.3 min·mg/L/mg, or a bioequivalent AUC (0-inf_D) in a range of 80% to 125%, or 80% to 120% of such reference AUC (0-inf_D).

In example embodiments, any of the described pharmaceutical dosage forms can be characterized by providing mean pharmacokinetic parameters upon oral dosing, fasted, of: Tmax 183±90 minutes, Cmax 3.5±1.7 mg/L, and/or AUC (0-inf_D) 1.08±0.46 min*mg/L/mg, or a bioequivalent Tmax, Cmax or AUC in a range of 80% to 125%, or 80% to 120% of such reference parameter.

In example embodiments, any of the described pharmaceutical dosage forms can be characterized by providing mean pharmacokinetic parameters upon oral dosing of the whole capsule, fasted, of: Tmax 194±38 minutes, Cmax 2.3±0.6 mg/L, and/or AUC (0-inf_D) 0.84±0.19 min*mg/L/mg, or a bioequivalent Tmax, Cmax or AUC in a range of 80% to 125%, or 80% to 120% of such reference parameter; and/or mean pharmacokinetic parameters upon oral dosing of the beads, sprinkled on applesauce, of: Tmax 190±61 minutes, Cmax 2.3±0.7 mg/L, and/or AUC (0-inf_D) 0.85±0.21 min*mg/L/mg, or a bioequivalent Tmax, Cmax or AUC in a range of 80% to 125%, or 80% to 120% of such reference parameter.

In another embodiment, the pharmaceutical dosage form is characterized by being bioequivalent when administered orally, fasted, in a hard capsule shell compared to the beads being administered orally, fasted, without a capsule shell. For example, the pharmaceutical dosage form can be characterized by the dosage form when administered orally in a hard capsule shell exhibiting a Cmax in a range of 80% to 125%, or 80% to 120%, of Cmax exhibited by the beads administered orally without a capsule shell. In another embodiment, the dosage form can be characterized by the dosage form when administered orally in a hard capsule shell exhibiting an AUC (0-12 h) or AUC (0-inf) in a range of 80% to 125%, or 80% to 120%, of that exhibited by the beads administered orally without a capsule shell, respectively. In one embodiment, both the Cmax and the AUC are within the tolerance ranges just described.

Purity

In one type of embodiment, the dosage form is characterized by having less than 5 wt. % cystamine, based on the amount of cysteamine, as determined by reverse phase HPLC with UV detection, as described herein. In other embodiments, the dosage form is characterized by having less than 5 wt. % cystamine, based on the amount of cysteamine, following 12 months storage at 25° C. and 40% relative humidity (RH), optionally as determined by reverse phase HPLC with UV detection, as described herein. In another type of embodiment, the dosage form is characterized by having less than 5 wt. % cystamine, based on the amount of cysteamine, following 18 months storage at 25° C. and 40% RH optionally as determined by reverse phase HPLC with UV detection, as described herein. In another type of embodiment, the dosage form is characterized by having less than 5 wt. % cystamine, based on the amount of cysteamine, following 24 months storage at 25° C. and 40% RH optionally as determined by reverse phase HPLC with UV detection, as described herein. In another type of embodiment, the dosage form is characterized by having less than 5 wt. % cystamine, based on the amount of cysteamine, following 30 months storage, or more, at 25° C. and 40% RH optionally as determined by reverse phase HPLC with UV detection, as described herein. Examples of suitable reverse phase HPLC assays are described herein.

In another type of embodiment, the dosage form is characterized by having less than 5 wt. % cystamine, based on the amount of cysteamine, following 12 months storage at 25° C. and 60% RH, optionally as determined by reverse phase HPLC with UV detection, as described herein. In another type of embodiment, the dosage form is characterized by having less than 5 wt. % cystamine, based on the amount of cysteamine, following 18 months storage at 25° C. and 60% RH, optionally as determined by reverse phase HPLC with UV detection, as described herein. In another type of embodiment, the dosage form is characterized by having less than 5 wt. % cystamine, based on the amount of cysteamine, following 24 months storage, or more, at 25° C. and 60% RH, optionally as determined by reverse phase HPLC with UV detection, as described herein.

In another type of embodiment, the dosage form is characterized by having less than 5 wt. % cystamine, based on the amount of cysteamine, following 3 months storage at 40° C. and 75% RH, optionally as determined by reverse phase HPLC with UV detection, as described herein. In another type of embodiment, the dosage form is characterized by having less than 5 wt. % cystamine, based on the amount of cysteamine, following 6 months storage at 40° C. and 75% RH, optionally as determined by reverse phase HPLC with UV detection, as described herein.

Any of the foregoing embodiments can be further characterized by having less than 8 wt. % total related substances (impurities) based on the amount of cysteamine, under the described storage conditions and times based on reverse phase HPLC with UV detection, as described herein.

Method of Making

Also contemplated is a method for the preparation of a dosage form according to the disclosure here, including coating a core particle comprising cysteamine or a pharmaceutically acceptable salt thereof and an excipient with an enteric polymer to form the enteric membrane.

The core particle including cysteamine or a pharmaceutically acceptable salt thereof can be formed by any suitable process. In one embodiment, the core particle is formed by granulating a mixture of cysteamine or a pharmaceutically acceptable salt thereof with an excipient and milling to a desired particle size range. In another embodiment, the core particle can be formed by extrusion and spheronization of a mixture of cysteamine or a pharmaceutically acceptable salt thereof with an excipient. Granulating processes can include fluid bed granulation, wet granulation, hot melt granulation, and spray congealing, for example. Other processes include slugging and roller compaction. As it is known in the art, the mixtures which are to be granulated can first be dry-blended. The dry-blended dry ingredients can be mixed with water, prior to extrusion.

It has been found that extrusion and spheronization of a mixture of cysteamine or a pharmaceutically acceptable salt thereof with an excipient can provide desirable core particles with a distribution of particle sizes as described herein and one or more other desirable properties. Cysteamine bitartrate oxidizes in air and in water, and with heat. Thus, short processing times can lead to a more stable product. For example, reducing the amount of spheronization reduces the amount of friction and related heat. For example, reducing the amount of time that the product is exposed to air (either in the moist state and/or before packaging) also reduces the amount of oxidation. On the other hand, rapid processing by extrusion and spheronization can lead to a poor quality product, for example in having a large fraction of the pellet cores falling outside a desired particle size range. The amount of moisture absorbed by spheronization aids (which does not happen immediately, but instead over time) influences the spheronization characteristics of the beads. Accordingly, it was determined that the moisture content of the wet mass, the related wet hold time for swelling of spheronization aid(s), and the spheronization time are parameters that can be optimized to achieve both good product yield, for example in a particle size range described herein, while maintaining good stability, e.g. not more than 5 wt. % cystamine based on the amount of cysteamine, as described herein.

Accordingly, in one embodiment the moisture content of the granulation mixture, prior to drying, is in a range of about 20 wt. % to about 40 wt. %, or 25 wt. % to about 35 wt. %, or about 28 wt. % to about 32 wt. %, or at least about 28 wt. %, or at least about 28.5, or at least about 20 wt. % to about 40 wt. %, or at least about 25 wt. % to about 35 wt. %, or at least about 27 wt. % to about 31 wt. % or at least about 28.5 wt. % to about 31 wt. %.

The wet mass can be held for a period of time prior to extrusion, e.g. in order to allow the sphronization aid to swell with granulating fluid. The hold time can be at least 15 minutes, at least 30 minutes, at least 45 minutes, or at least 60 minutes, for example. The hold time can be in a range of about 15 minutes to about 120 minutes, or about 30 minutes to 100 minutes, or 60 minutes to 90 minutes, for example.

As described above in connection with description of the core particles, the method can include a step of sorting (e.g., by sieving) the core particles prior to enteric coating, to retain particles in a predetermined size range, for example sizes in a range of about 0.7 mm to about 2.8 mm, or about 0.7 mm to about 2.5 mm, or about 0.8 mm to about 1.7 mm, or any range described above in connection with the core particles.

As described above in connection with description of the beads, the method can include a step of sorting (e.g., by sieving) the beads after enteric coating, to retain particles in a predetermined size range, for example sizes in a range of about 0.7 mm to about 2.8 mm, or about 0.7 mm to about 2.5 mm, or about 0.8 mm to about 1.7 mm, or any range described above in connection with the core particles.

In an extrusion and spheronization process, the following optional features can be employed, individually or in one or more combinations thereof. Water can be used as a granulation agent. Microcrystalline cellulose can be used in the core particles as a spheronization aid. Hypromellose can be included in the core particles as a binder. The extrusion screen size can be 1.0 mm. The friction plate of the spheronizer can be cross-hatched. The friction plate of the spheronizer can be cross-hatched with a square pitch of at least 3 mm, or greater than 3 mm, or at least 4 mm, or greater than 4 mm, or in a range of about 3 mm to about 7 mm, or about 5 mm. The spheronization time can be less than about 5 minutes, or less than about 4 minutes, or less than about 3 minutes, or less than about 2 minutes, or up to 1 minute. The spheronized particles can include non-spherical particles (i.e. irregular shapes), e.g. a substantial fraction thereof, e.g. at least 20 wt. % or at least 30 wt. %, or at least 40 wt. % or at least 50 wt. % or at least 60 wt. %, or at least 70 wt. % thereof.

The beads and/or filled capsules can be stored with a desiccant. The beads and/or filled capsules can be stored with an oxygen absorber.

For example, one embodiment of the method combining various of the parameters described above includes a method for the preparation of a pharmaceutical dosage form including cysteamine beads, including forming a wet mass comprising cysteamine bitartrate and an excipient, optionally microcrystalline cellulose, with a moisture content in a range of in a range of about 20 wt. % to about 40 wt. %, extruding and spheronizing the wet mass including cysteamine bitartrate and excipient to make core particles, sorting the core particles to a target particle size range, optionally 0.7 mm to 2.5 mm, coating the sorted core particles with an enteric polymer to form including beads comprising a core particle and an enteric membrane, and sorting the bead particles to a target particle size range, optionally 0.7 mm to 2.5 mm.

Use/Administration

For administration of the dosage form, a total weight in the range of approximately 100 mg to 1000 mg (based on the free base) can be used. The dosage form can be orally administered to a patient suffering from a condition for which an cysteamine is indicated, including, but not limited to, cystinosis and other metabolic and neurodegenerative diseases including non-alcoholic fatty liver disease (NAFLD), Huntingon's disease, Parkinson's disease, Rett Syndrome and others, use as free radical and radioprotectants, and as heptoprotectant agents. In any method described herein, the treatment of humans is contemplated. The compositions of the disclosure can be used in combination with other therapies useful for treating cystinosis and neurodegenerative diseases and disorders. For example, indomethacin therapy (Indocid® or Endol®) is an anti-inflammatory used to treat rheumatoid arthritis and lumbago, but it can be used to reduce water and electrolyte urine loss. In children with cystinosis, indomethacin reduces the urine volume and therefore liquid consumption by about 30%, sometimes by half. In most cases this is associated with an appetite improvement. Indomethacin treatment is generally followed for several years.

Other therapies can be combined with the methods and compositions of the disclosure to treat diseases and disorders that are attributed or result from cystinosis. Urinary phosphorus loss, for example, entails rickets, and it may be necessary to give a phosphorus supplement. Carnitine is lost in the urine and blood levels are low. Carnitine allows fat to be used by the muscles to provide energy. Hormone supplementation is sometimes necessary. Sometimes the thyroid gland will not produce enough thyroid hormones. This is given as thyroxin (drops or tablets). Insulin treatment is sometimes necessary if diabetes appears, when the pancreas does not produce enough insulin. These treatments have become rarely necessary in children whom are treated with cysteamine, since the treatment protects the thyroid and the pancreas. Some adolescent boys require a testosterone treatment if puberty is late. Growth hormone therapy may be indicated if growth is not sufficient despite a good hydro electrolytes balance. Accordingly, such therapies can be combined with the compositions and methods disclosed herein.

The effectiveness of a method or composition of the disclosure can be assessed by measuring leukocyte cystine concentrations. Dosage adjustment and therapy can be made by a medical specialist depending upon, for example, the concentration of cystine in leukocytes and the ability to tolerate the drug. Additional therapies including the use of omeprazole (Prilosec®) can reduce side effects of cysteamine administration, such as abdominal pain, heartburn, nausea, vomiting, and anorexia, which can result from cysteamine-induced gastric acid hypersecretion, for example.

In addition, various prodrugs can be "activated" by use of the enterically coated cysteamine. Prodrugs are pharmacologically inert, they themselves do not work in the body, but once they have been absorbed, the prodrug decomposes. The prodrug approach has been used successfully in a number of therapeutic areas including antibiotics, antihistamines and ulcer treatments. The advantage of using prodrugs is that the active agent is chemically camouflaged and no active agent is released until the drug has passed out of the gut and into the cells of the body. For example, a number of prodrugs use S—S bonds. Weak reducing agents, such as cysteamine, reduce these bonds and release the drug. Accordingly, the compositions of the disclosure are useful in combination with pro-drugs for timed release of the drug. In this aspect, a pro-drug can be administered followed by administration of an enterically coated cysteamine composition of the invention (at a desired time) to activate the pro-drug.

EXAMPLES

The following examples are provided for illustration and are not intended to limit the scope of the invention.

Example 1

Bead Production

Cysteamine bitartrate and excipients (microcrystalline cellulose, hypromellose, sodium lauryl sulfate) were milled through a Comil equipped with a 0.094" (2.3876 mm) screen operating at 500 RPM. The amount of each ingredient (per 75 mg cysteamine capsule) is cysteamine bitartrate 258 mg+/−37.0 mg; microcrystalline cellulose 67.1 mg+/−9.6 mg; hypromellose 17.2 mg+/−2.5 mg; and sodium lauryl sulfate 1.75 mg+/0.25 mg. Cysteamine bitartrate was passed through the Comil first followed by the excipients (hypromellose 2910-5, sodium lauryl sulfate, and microcrystalline cellulose). Cysteamine bitartrate and the excipients were dry blended for approximately 15 minutes. While mixing at a setpoint speed of 47 rpm, purified water was slowly added (addition in approximately 4 minutes) into the blended components. After the water addition, the wet blend was mixed for an additional minute for a total of 5 minutes.

A sample of the wet blend was collected and moisture content was determined by loss on drying (LOD). The wet mass was discharged in polyethylene lined fiber drums and held for 60-90 minutes prior to extrusion/spheronization.

The granulated wet mass was loaded onto a NICA extruder equipped with a 1.0 mm screen at a feeder speed of 100 RPM setpoint and extruded at a setpoint speed of 55 RPM (50-60 RPM). The extruded product was immediately spheronized using a NICA Spheronizer equipped with 5.0 mm crosshatched friction plates. Spheronization was performed at a target speed of 625 RPM (500-700 RPM) for 40-60 seconds. The particles were collected in double polyethylene lined fiber drums and stored at room temperature for further processing.

The wet particles were dried in a Niro fluid bed dryer with an inlet air temperature setpoint of 70° C. (60-80° C.). Drying was complete when the moisture content of uncrushed particles reached ≤1.0% w/w by LOD. Sampling of the particles began when the outlet air temperature reached approximately 50° C. and continued until the acceptance criterion of ≤1.0%. The dried particles were transferred to fiber drums lined with double polyethylene bags and stored at room temperature.

The dried particles were screened through a #12 mesh screen and a #20 mesh screen. Particles passing through the #12 mesh and retained on the #20 mesh were collected as product in double polyethylene lined containers with desiccant and oxygen absorber packets in the outer liner. The collected product may be re-passed through the screens as needed. Particles greater than #12 mesh and less than #20 mesh were not retained as product for coating.

An enteric coating solution of Eudragit L30 D-55, triethyl citrate, and talc in purified water was prepared in a mixing tank equipped with a propeller mixer and placed on a balance. Eudragit L 30 D-55 was added to the portable mixing tank through a 60-mesh screen. The final solution was mixed for a minimum of 30 minutes and mixed continuously during the coating process. Based on a 75 mg cysteamine capsule, the amounts of coating ingredients were: Eudragit L30 D-55 66.2 mg+/−9.5 mg; triethyl citrate 6.65 mg+/−0.95 mg; talc 15.3 mg+/−2.2 mg.

Spray lines connecting the portable mixing tank to the Niro fluid bed dryer were primed. The floor balance was tared prior to starting the coating process. The amount of coating solution sprayed was calculated as the amount required to increase the core particle weight by 25%.

The core particles were loaded into the Niro fluid bed dryer equipped with a Precision Coater which sprays from the bottom, 1.0 mm Nozzle, 30 mm Swirl Accelerator, and 300 µm Filter Bonnet. The coating process parameters are provided in the table below.

| Parameter | Setpoint | Range |
| --- | --- | --- |
| Inlet Air Volume | 450 scfm | 300-600 scfm |
| Inlet Air Temperature | 60° C. | 45-75° C. |
| Product Temperature | 30° C. | 25-45° C. |
| Solution Spray Rate | 0.220 kg/minute | 0.200-0.240 kg/minute |
| Atomization Air Pressure | 36 psi | 32-40 psi |

Once the target weight of coating solution was applied (25% of dry particle weight), the beads were weighed to confirm weight increase of ≥25.0%. If the weight was not ≥25.0% of the uncoated particle weight, the coating process was continued until ≥25.0% was achieved.

The coated beads were dried at an inlet temperature setpoint of 45° C. (35-55° C.) and inlet air volume setpoint of 350 scfm (300-400 scfm) until the LOD of the coated beads was ≤2.0% w/w. Once the LOD was reached, the inlet air heating was turned off and the beads were circulated at an air inlet volume of 300-400 scfm until the product temperature reached not more than (NMT) 30° C.

The weight gain of the dried coated beads was calculated to confirm a maximum weight gain of ≤31.0% was achieved. Visual inspection confirmed that the enteric membrane thickness was not consistent bead-to-bead, but instead there was a distribution of enteric membrane thicknesses.

The dried coated beads were screened through a #12 mesh and a #20 mesh screen in sequence. Beads passing through the #12 mesh screen and retained on the #20 mesh screen were collected as product in double polyethylene lined fiber drums with a desiccant and oxygen absorber canister in the outer liner. Mesh analysis testing can be performed as an in-process test to confirm the beads are within the limits of: NMT 5% are retained on a #12 mesh screen (1.68 mm) and NMT 10% pass through a #20 mesh screen (0.84 mm). If results are not within the limits, the product can be sorted by rescreening until the mesh analysis results meet the specified limits.

The dried coated beads were lubricated with talc prior to encapsulation. The coated beads were loaded in a V-blender; talc powder was added to the coated beads (calculated as 0.5% w/w of the total coated bead weight). The contents were mixed for a minimum of five minutes. The lubricated coated beads were transferred to double polyethylene lined fiber drums with desiccant and oxygen absorber packets in the outer liner and stored at room temperature. Lubricated coated beads were used in the manufacture of 75 mg size 0 capsules and 25 mg size 3 capsules. One batch of coated beads can be filled as a 75 mg strength batch or can be split to fill both 75 mg and 25 mg strengths, for example.

The 75 mg hard gelatin capsules were filled using an automated encapsulator at a speed of 80-100 spm to the target fill weight calculated to achieve 75 mg cysteamine free base per capsule. The 25 mg hard gelatin capsules were also filled with an automated encapsulator at a speed of 50-70 spm. The beads were introduced into the encapsulation process with a hopper.

Example 2

Particle Size Distribution

Several lots of cysteamine bitartrate enteric-coated beads produced via an extrusion and spheronization process as described herein were analyzed for particle size distribution via analytical sieving. The results are tabulated below.

| Sieve Size (µm) | % Retained Lot A | % Retained Lot B | % Retained Lot C | % Retained Lot D |
|---|---|---|---|---|
| 1700 | 0 | 0 | 0 | 0 |
| 1400 | 1.4 | 3.2 | 3.2 | 1.2 |
| 1180 | 19.5 | 25.7 | 26.7 | 20.3 |
| 1000 | 61.9 | 55.5 | 56 | 62 |
| 850 | 16.1 | 14.2 | 13.5 | 15.1 |
| <850 | 1.2 | 1.4 | 0.6 | 1.4 |

Example 3

Pharmacokinetics

A population PK study was performed using Cystagon® and capsules of cysteamine bitartrate gastro-resistant beads (CBGB) produced according to the method of Example 1 herein.

Pharmacokinetic (PK) and pharmacodynamic (PD) relationships following a single dose of CBGB capsules was first studied in comparison to a single dose of immediate-release cysteamine bitartrate in a study with 9 patients. Following normalization to a 450 mg dose, the maximum plasma levels C max, AUC 0-6 h and AUC 0-12 h (calculated directly from the plasma level data for CBGB and from doubling the AUC 0-6 h value for immediate-release cysteamine to represent two doses) were lower for CBGB (27.70±14.99 µmol/L, 75.93±39.22 µmol*h/L and 99.26±44.21 µmol*h/L respectively) than for immediate-release cysteamine bitartrate (37.72±12.10 µmol/L, 96.00±37.81 µmol*h/L and 192.00±75.62 µmol*h/L respectively. The pharmacokinetics of CBGB are consistent with a delayed-release formulation showing a T max of 2.78±1.56 h for CBGB cysteamine was moderately bound to human plasma proteins, predominantly to albumin, with mean protein binding of about 52%. Plasma protein binding was independent of concentration over the concentration range achieved clinically with the recommended doses.

Additional studies were carried out as follows.

CBGB-A Study

Cystagon® Treatment Assignment: one (1) pre-dose PD sample was collected at time 0 (i.e., within 15 minutes prior to the morning Cystagon® dose administration), considered as the time of trough cysteamine/peak of WBC cystine after administration of immediate-release cysteamine bitartrate (Cystagon®). One (1) additional PD sample was collected at a sample timepoint that was time-matched to 1 of 3 PK sample profile times (either 2, 4 or 6 hours) post morning Cystagon® dose. There were six associated plasma PK samples collected at time 0 (within 15 minutes prior to morning Cystagon® dose); 30 minutes post morning Cystagon® dose; and 1, 2, 4 and 6 hours (immediately prior to the afternoon Cystagon® dose)

Inventive capsule Treatment Assignment: one (1) post-dose PD sample was collected at time 0.5 hour (30 minutes), considered as the time of trough cysteamine/peak of WBC cystine after administration of capsules of CBGB. Two (2) additional PD samples were collected at sample timepoints that were time-matched to PK sample profile times (either 3, 4, 8, 10 or 12 hours) post morning CBGB dose. In order to limit the impact of autocorrelation, juxtaposed times of sampling for patients treated with CBGB were not to be taken into account for the randomization. Therefore, patients were randomized to one of the following six pairs of the sampling time points: 3 and 8 hours, 3 and 10 hours, 3 and 12 hours, 4 and 8 hours, 4 and 10 hours, 4 and 12 hours. There were nine associated plasma PK samples collected at time 0 (within 15 minutes prior to morning CBGB dose), 30 minutes, 2, 3, 4, 6, 8, 10 and 12 hours post morning CBGB dose (immediately prior to the evening CBGB dose).

As recommended in the Cystagon® SmPC, food (meal or snack) was available 30 minutes prior to receiving the morning dose and (if applicable) the next Q6H of Cystagon® administration and the morning dose and Q12H CBGB administration and (if applicable) the next Q12H CBGB dose. Cystagon® was administered with water and CBGB was administered with an acidic beverage. Dairy products should have been withheld 1 hour before and after CBGB dosing.

CBGB-B Study

Administering cysteamine in fasted healthy volunteers provides very stable PK parameters such that it was possible to demonstrate bioequivalence between administrations of CBGB capsules as a whole or as their content sprinkled on food with only 20 healthy volunteers.

The PK parameters of cysteamine were determined after a single dose, first in fasted healthy volunteers, then in patients at steady state, using the model parameters obtained with healthy volunteers as starting parameters for the models in patients. Pharmacokinetic modeling of cysteamine was based on a 2-compartment model and pharmacodynamic modeling of WBC cystine was based on an inhibitory $E_{max}$ model. (Belldina, E. B., M. Y. Huang, et al. (2003). "Steady-state pharmacokinetics and pharmacodynamics of cysteamine bitartrate in paediatric nephropathic cystinosis patients." Br J Clin Pharmacol 56(5): 520-525.)

Since CBGB studies in healthy volunteers were not done against Cystagon®, data in fasted healthy volunteers (Gangoiti, J. A., M. Fidler, et al. (2010). "Pharmacokinetics of enteric-coated cysteamine bitartrate in healthy adults: a pilot study." Br J Clin Pharmacol 70(3): 376-382) were used to determine initial PK model parameters for Cystagon®. And data on EC-cysteamine (i.e. Eudragit L50D 55 enteric-coated capsules of Cystagon®—a different way of providing delayed-release cysteamine bitartrate) in this dataset was used for comparison purposes.

A bioequivalence designed to demonstrate bioequivalence between oral administration of intact CBGB capsules, and contents of opened CBGB capsules mixed with applesauce and taken orally. Twenty (20) healthy adults (mean age 37 years, range 19-64 years) received both presentations, 8 (75 mg) intact vs. 8 (75 mg) open capsules, in a crossover design study.

The final results are presented in the table below.

| Study/Protocol Country | Study Design | No. Subjects Entered/Completed (M/F) | HV/P[a] (Age: Mean, Range) | Treatment | Dose (mg) | Non-Compartmental Analysis (Pharsight, WinNonLin 6.2) | | | Population PK, 2-compartment Model (Pharsight, NLME 1.1) | | | | | |
|---|---|---|---|---|---|---|---|---|---|---|---|---|---|---|
| | | | | | | $T_{max}$ (min) | $C_{max}$ (mg/L) | $C_{max}$_D (mg/L/mg) | $AUC_{inf}$_D (min*mg/L/mg) | $T_{lag}$ (min) | Ka (1/min) | V/F (L) | Cl/F (L/min) | $V_2$ (L) | $Cl_2$ (L/min) |
| UCSD (USA) | Open label, Sequential | (4M/3F)/ (4M/3F) | P (12, 8-17) | Cystagon® | 450 | 75 ± 19 | 3.1 ± 1.2 | 0.007 ± 0.003 | 0.88 ± 0.30 | 26 | 0.029 | 73 | 1.07 | 131 | 0.41 |
| | | | | EC-Cysteamine | 450 | 220 ± 74 | 3.2 ± 1.4 | 0.007 ± 0.003 | 0.96 ± 0.40 | 156 | 0.025 | 98 | 1.17 | 54 | 0.5 |
| CBGB-A (USA/EU) | Random, Crossover | (24M/19F)/ (22M/16F) | P(12, 6-26) | Cystagon® | 250-750 | 74 ± 32 | 2.6 ± 1.4 | 0.006 ± 0.003 | 0.84 ± 0.31 | 23 | 0.025 | 94 | 1.1 | 191 | 0.5 |
| | | | | CBGB caps | 425-1300 | 183 ± 90 | 3.5 ± 1.7 | 0.005 ± 0.002 | 1.08 ± 0.46 | 60 | 0.015 | 87 | 1.2 | 200 | 0.4 |
| CBGB-B (USA) | Random, Crossover | (13M/7F)/ (13M/7F) | HV(37, 19-64) | CBGB caps | 600 | 194 ± 38 | 2.3 ± 0.6 | 0.004 ± 0.001 | 0.84 ± 0.19 | 95 | 0.016 | 137 | 1.4 | 187 | 0.44 |
| | | | | CBGB sprinkled | 600 | 190 ± 61 | 2.3 ± 0.7 | 0.004 ± 0.001 | 0.85 ± 0.21 | 98 | 0.017 | 151 | 1.4 | 192 | 0.47 |

[a]HV = Healthy Volunteers, P = Patients

The conclusion of this population PK modeling on two different presentations of CBGB (open and intact), is that the only difference between administering CBGB as intact capsules and as open capsules, sprinkled on applesauce, is expressed by the difference between lag times: as expected the start of absorption from the beads is still delayed (85 min) but slightly less than when the gelatin capsule has to be dissolved first (108 min) and this has not much of an impact on $T_{max}$ (190 min for open capsules vs. 194 min for intact capsules) since probably only a small amount of beads dissolves early.

However, comparison between the two presentations of CBGB (open and intact) and the immediate-release cysteamine bitartrate (Cystagon®) and the delayed-release EC-cysteamine, shows that the absorption of cysteamine after CBGB dosing is not only more delayed (Cystagon® $T_{lag}$<<CBGB $T_{lag}$<<EC-cysteamine $T_{lag}$) but also further extended due to a slower absorption (CBGB $K_a$<<Cystagon® $K_a$≈EC-cysteamine $K_a$) compared to EC-cysteamine. Without intending to be bound by any particular theory, it is contemplated that the difference in absorption of the CBGB formulation is related to one or more factors including the distribution of bead sizes and time-progressive dissolution of multiple beads and/or the irregularity of bead shapes in the CBGB formulation and/or the distribution of enteric membrane thicknesses in the CBGB formulation.

Example 4

Purity and Stability

Long term stability tests have been performed on the CBGB formulation made according to Example 1. The major impurity in the CBGB product is cystamine, the well known related substance (dimer).

The use of a more sensitive and less selective method has resulted in the observation of several impurities found in the CBGB formulation and the commercial product using cysteamine bitartrate, Cystagon®. Through the use of reverse phase HPLC, six peaks observed in the CBGB formulation related substances chromatograms have been identified as product degradants (specifically cysteamine bitartrate degradants). Two lots of Cystagon® were evaluated by the same test method. The impurities observed in representative CBGB chromatograms are also observed in Cystagon®.

Impurities Assay Method

Cysteamine bitartrate samples are assessed by gradient elution HPLC using an XBRIDGE C18 column (dimensions: 150 mm×4.6 mm; packing particle size: 3.5 µm) (Waters, Milford, Mass.). The autosampler temperature is 4° C. Approximately 10 µL or approximately 100 µL of sample is injected onto the column. The column temperature is 40° C. and the sample is eluted at a flow rate of 1.0 mL/min according to the following profile:

| HPLC Gradient | | |
|---|---|---|
| Time (min) | Mobile Phase A (%) | Mobile Phase B (%) |
| 0.0 | 100 | 0 |
| 2.0 | 100 | 0 |
| 20.0 | 60 | 40 |
| 25.0 | 60 | 40 |
| 25.1 | 100 | 0 |
| 40.0 | 100 | 0 |

Mobile Phase A contains 23.6 mM 1-octanesulfonic acid sodium and 29.0 mM sodium phosphate (pH 2.6)/acetonitrile/methanol 85/3/12 (v/v/v). Mobile Phase B contains 0.20 M 1-octanesulfonic acid sodium and 0.10 M sodium phosphate (pH 2.6)/acetonitrile/methanol 10/18/72 (v/v/v). The purity of 1-octanesulfonic acid is ≥98%. Detection is carried out using a UV detector at 210 nm.

Reference Solution Preparation.

Reference solutions of Cysteamine Bitartrate Analytical Reference Standard are prepared as follows. Working Standard and Working Check Standard solutions are prepared having a nominal concentration of 0.54 mg/mL Cysteamine Bitartrate Analytical Reference Standard in Mobile Phase A using low actinic glassware. A Working Sensitivity solution is prepared having a nominal concentration of 0.30 mg/mL Cysteamine Bitartrate Analytical Reference Standard in Mobile Phase A using low actinic glassware, which corresponds to the limit of quantification (LOQ) for cysteamine. The water content of the Cysteamine Bitartrate Analytical Reference Standard is determined no more than 7 days before use by Karl Fischer titration or thermal gravimetric analysis (TGA). The Reference Standard is stored refrigerated and blanketed under nitrogen.

Bead Prep Assay Sample Preparation.

Cysteamine Bitartrate Gastro-resistant Beads (CBGB) are prepared for analysis according to the following procedure. About 3.7 g of CBGB beads are ground to a fine powder using a ball mill for approximately 1 minute at 27 Hz. The grind is transferred to an amber bottle for storage. Stock Bead Prep Assay sample solutions are prepared in duplicate by adding 370.4 mg±5 mg of the grind to a 250 mL low actinic volumetric flask and diluting with Mobile Phase A. The mixture is stirred with a stir bar for at least 15 minutes. Approximately 15 mL of the resulting solution is filtered through a 0.45 µm nylon filter, with the first 5 mL being discarded. The cysteamine concentration of the resulting Stock Bead Prep Assay sample solution is approximately 0.300 mg/mL. Working Bead Prep sample solutions are prepared by placing 4.0 mL of Stock Bead Prep Assay sample solution in a 25 mL low actinic volumetric flask and diluting to volume with Mobile Phase A. The cysteamine concentration of the resulting Working Bead Prep sample solution is approximately 0.048 mg/mL.

Assay Sample Preparation.

CBGB capsules are prepared for analysis according to the following procedure. To reduce exposure to light and oxygen, sample preparation (from the initial weighing of the full capsules to the loading of sample vials on the HPLC) is completed in one day. Ten capsules are weighed. The capsule contents are emptied and the empty shells are weighed to determine the average capsule fill weight. The capsule contents are ground to a fine powder using a ball mill for approximately 1 minute at 27 Hz. The grind is transferred to an amber bottle for storage. Stock sample solutions are prepared in duplicate by adding the appropriate amount of the grind for 1 capsule (as determined by the average capsule fill weight) to a 25 mL low actinic volumetric flask and diluting with Mobile Phase A. The mixture is stirred with a stir bar for at least 15 minutes. The resulting solution is centrifuged at about 3400 rpm for 5 minutes. Approximately 15 mL of the centrifuged solution is filtered through a 0.45 µm nylon filter (Acrodisc, 25 mm diameter), with the first 5 mL being discarded, to obtain Stock sample solutions. Working sample solutions are prepared by placing 6.0 mL of Stock sample solution (for 25 mg capsules) or 2.0 mL of Stock sample solution (for 75 mg capsules) in a 10 mL low actinic volumetric flask and diluting to volume with Mobile Phase A.

Content Uniformity Sample Preparation.

CBGB capsules are prepared for analysis according to the following procedure. To reduce exposure to light and oxygen, sample preparation (from the initial weighing of the full capsules to the loading of sample vials on the HPLC) is completed in one day. Ten capsules are weighed. The contents of each capsule are emptied into separate mortars and the empty shells are weighed to determine the individual capsule fill weight. About 1-2 mL of Mobile Phase A is added into the mortar. The beads are immediately ground to a paste. If needed, additional Mobile Phase A is added to the paste, up to 5 mL total. The paste is transferred to a 250 mL low actinic volumetric flask. The mortar and pestle are thoroughly rinsed with Mobile Phase A and the rinse solution is collected in to the same flask. The flask is filled about three-quarters full with Mobile Phase A and stirred for at least 15 minutes. The flask is filled to volume with Mobile Phase A. Approximately 20 mL of the resulting solution is filtered through a 0.45 µm nylon filter (Acrodisc, 25 mm diameter), with the first 5 mL being discarded, to obtain Stock CU sample solutions. Working CU sample solutions are prepared by placing 12.0 mL of Stock CU sample solution (for 25 mg capsules) or 4.0 mL of Stock CU sample solution (for 75 mg capsules) in a 25 mL low actinic volumetric flask and diluting to volume with Mobile Phase A. The cysteamine concentration of the resulting Working CU sample solutions is approximately 0.048 mg/mL.

Data Analysis.

The cysteamine Working Standard solution concentration is calculated according to the following equation: Cysteamine Concentration ($C_{Std}$)=mg Cysteamine Bitartrate Analytical Reference Standard×$P_f$/25.0 mL $P_f$ represents a purity factor for the standard material. $P_f$ is calculated according to the following equation:

$$P_f = B \times (100 - \text{Water}) \times C/100$$

where B=the anhydrous cysteamine free base in the Cysteamine Bitartrate Analytical Reference Standard (expressed as a decimal value on the standard bottle label),
water=the water content as determined by Karl Fischer or TGA no more than 7 days before use (expressed as a percentage), and
C=the cystamine correction (expressed as a decimal value on the standard bottle label).

The amount of cysteamine per capsule is calculated according to the following equation:

$$\text{mg cysteamine per capsule} = (A_{Sam}/A_{Std}) \times C_{Std} \times \text{DF} \times (\text{AveWt/SamWt})$$

where $A_{Sam}$=the peak area of cysteamine in the sample chromatogram with a 10 µL injection,
$A_{Std}$=the average peak area of cysteamine in all Working Standard solution chromatograms with a 10 µL injection,
$C_{Std}$=the concentration (mg/mL) of cysteamine in the Working Standard solution,
DF=the dilution factor (125 for 75 mg capsules; 41.6667 for 25 mg capsules),
AveWt=the average capsule fill weight (mg), and
SamWt=the sample weight (mg).

For Content Uniformity, the amount of cysteamine per capsule is calculated according to the following equation:

$$\text{mg cysteamine per capsule} = (A_{Sam}/A_{Std}) \times C_{Std} \times \text{DF}$$

where $A_{Sam}$=the peak area of cysteamine in the sample chromatogram with a 10 µL injection,
$A_{Std}$=the average peak area of cysteamine in all Working Standard solution chromatograms with a 10 µL injection,
$C_{Std}$=the concentration (mg/mL) of cysteamine in the Working Standard solution, and
DF=the dilution factor (1562.5 for 75 mg capsules; 520.8 for 25 mg capsules).

For the Bead Prep Assay, the amount of cysteamine per capsule is calculated according to the following equation:

$$\text{mg cysteamine per capsule} = (A_{Sam}/A_{Std}) \times C_{Std} \times \text{DF} \times (\text{AveWt/SamWt})$$

where $A_{Sam}$=the peak area of cysteamine in the sample chromatogram with a 10 µL injection,
$A_{Std}$=the average peak area of cysteamine in all Working Standard solution chromatograms with a 10 µL injection,
$C_{Std}$=the concentration (mg/mL) of cysteamine in the Working Standard solution,
DF=the dilution factor (use the 75 mg Dilution Factor, 1562.5),
AveWt=the average capsule fill weight (mg) (use the target fill weight, 370.4 mg), and
SamWt=the sample weight (mg) (use the actual weight used in sample preparation).

The percentage of the label claim (% LC) is calculated for the Assay, Content Uniformity, and Bead Prep Assay sample solutions according to the following equation:

$$\%LC = (\text{mg cysteamine})/LC \times 100\%$$

where mg cysteamine=the amount calculated by the applicable equation above, and
LC=the amount of the label claim (75 mg or 25 mg) (use 75 mg for the Bead Prep Assay).

The amount of substances related to cysteamine bitartrate (including cysteamine impurities) such as cystamine is calculated according to the following equation:

$$\text{mg related substance} = (A_{RS}/A_{Std}) \times (C_{Std}/RRF) \times DF \times (\text{AveWt}/\text{SamWt})$$

where $A_{RS}$=the peak area of any related substance in the Working sample solution chromatogram with a 100 μL injection (peaks before RRT 0.48 are disregarded; peaks observed in the chromatogram of the second injection of Mobile Phase A/Blank (100 μL injection) are also disregarded),
$A_{Std}$=the average peak area of cysteamine in all Working Standard solution chromatograms with a 10 μL injection,
$C_{Std}$=the concentration (mg/mL) of cysteamine in the Working Standard solution,
RRF=the relative response factor (0.98 for cystamine; 1.00 for other related substances),
DF=the dilution factor (12.5 for 75 mg capsules; 4.16667 for 25 mg capsules),
AveWt=the average capsule fill weight (mg), and
SamWt=the weight the sample grind from the Working sample solution preparation (mg).

The weight percentage of cystamine and other individual related substances is determined according to the following equation:

$$\%\text{ individual related substance} = \text{mg related substance}/\text{mg cysteamine} \times 100\%$$

where mg related substance=the amount of related substance calculated above, and
mg cysteamine=the amount of cysteamine for the Assay sample.

The percentage of total related substances is determined by summing all related substances greater than or equal to 0.05%. Peaks after 28 minutes are disregarded. In contrast to a previous electrochemical detection method that disregarded early-eluting peaks as not relevant to the purity calculation, the foregoing method determines that early peaks are impurities and integrates early-eluting peaks as described above.

Results

Two lots of Cystagon® were dispensed in standard pharmacy containers and verified to be well within the manufacturer's expiration date. One lot was provided by a healthcare provider. It was dispensed in a standard pharmacy bottle and verified by the healthcare provider to be well within the expiration date. Upon analysis by the Test Method, it was shown to contain 9.1% cystamine by weight and 10.3% total related substances, based on the weight of cysteamine, using the assay described above. The second analyzed Cystagon® lot was identified by lot number. Upon analysis by the assay described above, it was shown to contain 5.2% cystamine by weight and 5.7% total related substances, based on the weight of cysteamine. Each Cystagon® lot was shipped and stored under specified label conditions.

Two representative lots of the CBGB capsule formulation were analyzed by the assay described above and were shown to contain 3.7% cystamine by weight and 3.6% cystamine by weight, respectively, based on the weight of cysteamine, at the time of manufacture. For both lots, the total amount of related substances was 4.2% by weight, based on the weight of cysteamine.

The CBGB product lots were put on stability testing in various packages and storage conditions, then assayed for purity using the assay described above. The results are shown in the table below

| Lot | Product dose/count/ bottle size | Conditions °C./% RH | Cystamine %/total related substances at time point (month) | | | | | | |
|---|---|---|---|---|---|---|---|---|---|
| | | | Initial | 1 | 2 | 3 | 6 | 9 | 12 |
| 1 | 75 mg/60/100 cc | 25/60 | 3.7/4.2 | 3.7/NA | 3.1/NA | 3.4/4.2 | 3.5/4.4 | 3.7/5.1 | 3.8/5.5 |
| 1 | 75 mg/60/100 cc | 40/75 | 3.7/4.2 | 3.7/NA | 3.2/NA | 3.5/7.9 | 3.9/12.3 | | |
| 1 | 75 mg/150/250 cc | 25/60 | 3.7/4.2 | 3.5/NA | 3.4/NA | 3.7/4.5 | 3.6/4.3 | 3.6/4.9 | 3.7/5.4 |
| 1 | 75 mg/150/250 cc | 40/75 | 3.7/4.2 | 3.4/NA | 3.4/NA | 3.7/7.9 | 3.8/11.6 | | |
| 1 | 75 mg/300/400 cc | 25/60 | 3.7/4.2 | 3.5/NA | 3.3/NA | 3.4/4.2 | 3.5/4.4 | 3.7/5.1 | 3.8/5.7 |
| 1 | 75 mg/300/400 cc | 40/75 | 3.7/4.3 | 3.4/NA | 3.2/NA | 3.6/7.7 | 4.0/12.8 | | |
| 1 | 75 mg/60/bulk | 25/40 | 3.7/4.2 | 3.4/NA | 3.4/NA | 3.2/NA | 3.3/4.2 | 3.3/4.5 | 3.2/4.6 |
| 1 | 75 mg/60/bulk | 40/75 | 3.7/4.2 | 3.4/NA | 3.2/NA | 3.3/NA | 2.9/9.1 | | |
| 2 | 75 mg/150/250 cc | 25/60 | 3.6/4.2 | 3.1/4.0 | 3.3/4.3 | 3.0/4.3 | 3.3/5.0 | | |
| 2 | 75 mg/150/250 cc | 40/75 | 3.6/4.2 | 3.1/7.5 | 3.6/12.1 | | | | |

Additional CBGB product samples according to Example 1 were put on long term stability testing in various packages and storage conditions, then assayed for purity using the assay described above. Results are shown in the table below.

| Lot | Product dose/count/bottle size | Conditions °C./% RH | Cystamine %/total related substances at time point (month) | | | | | | | | | |
|---|---|---|---|---|---|---|---|---|---|---|---|---|
| | | | Initial | 1 | 2 | 3 | 6 | 9 | 12 | 15 | 18 | 24 |
| 3 | 25 mg/60/50 cc | 25/60 | 3.2/4.1 | 3.0/NA | 3.3/NA | 3.1/4.2 | 3.3/4.7 | 3.2/4.9 | 3.6/5.5 | NA | 4.0/6.8 | 4.6/NA |
| 3 | 25 mg/60/50 cc | 40/75 | 3.2/4.1 | 2.9/NA | 3.0/NA | 3.0/7.8 | 3.7/13.4 | | | | | |

-continued

| Lot | Product dose/count/bottle size | Conditions °C./% RH | Cystamine %/total related substances at time point (month) | | | | | | | | | |
|---|---|---|---|---|---|---|---|---|---|---|---|---|
| | | | Initial | 1 | 2 | 3 | 6 | 9 | 12 | 15 | 18 | 24 |
| 4 | 75 mg/150/250 cc | 25/60 | 3.2/4.0 | 3.2/NA | 3.4/NA | 3.4/4.7 | 3.7/5.2 | 3.5/5.3 | 4.1/6.3 | NA | 4.2/7.1 | 4.7/NA |
| 4 | 75 mg/150/250 cc | 40/75 | 3.2/4.0 | 3.1/NA | 3.4/NA | 3.5/9.0 | 4.0/13.8 | | | | | |
| 5 | 75 mg/60/100 cc | 25/60 | 3.4/4.2 | 3.4/NA | 3.5/NA | 3.3/4.4 | 3.7/5.2 | 3.5/5.2 | 5.0/NA | 3.9/6.0 | 3.9/NA | 5.3/NA |
| 5 | 75 mg/60/100 cc | 40/75 | 3.4/4.2 | 3.3/NA | 3.4/NA | 3.3/8.5 | 4.1/16.0[1] | | | | | |
| 5 | 75 mg/300/400 cc | 25/60 | 3.4/4.2 | 3.5/NA | 3.5/NA | 3.5/4.9 | 4.0/6.0 | 3.3/5.3 | 5.3/NA | 4.1/6.5 | 4.1/NA | 5.3/NA |
| 5 | 75 mg/300/400 cc | 40/75 | 3.4/4.2 | 3.5/NA | 3.7/NA | 3.7/9.6 | 4.2/15.4[1] | | | | | |
| 5 | 75 mg/60/bulk | 25/60 | 3.4/4.2 | 3.5/NA | 3.5/NA | 3.4/NA | 3.7/5.2 | 3.2/NA | 4.1/5.5 | | | |
| 5 | 75 mg/60/bulk | 40/75 | 3.4/4.2 | 3.4/NA | 3.4/NA | 3.1/NA | 3.0/11.2 | | | | | |
| 6 | 25 mg/60/50 cc | 25/60 | 3.3/4.1 | 3.3/NA | 3.2/NA | 3.2/4.3 | 3.7/5.5 | 3.3/5.0 | 4.0/NA | 3.9/5.9 | 4.4/NA | 5.1/NA |
| 6 | 25 mg/60/50 cc | 40/75 | 3.3/4.1 | 3.2/NA | 3.1/NA | 3.0/7.8 | 3.8/15.7[1] | | | | | |
| 6 | 25 mg/420/250 cc | 25/60 | 3.3/4.1 | 3.3/NA | 3.5/NA | 3.6/4.9 | 4.0/6.0 | 3.8/5.9 | 4.6/NA | 4.8/7.4 | 4.1/NA | 5.2/NA |
| 6 | 25 mg/420/250 cc | 40/75 | 3.3/4.1 | 3.4/NA | 3.5/NA | 3.5/9.7 | 4.7/17.1[1] | | | | | |
| 6 | 25 mg/60/bulk | 25/60 | 3.3/4.1 | 3.4/NA | 3.4/NA | 3.3/NA | 3.7/5.4 | 3.1/NA | 3.5/5.3 | | | |
| 6 | 25 mg/60/bulk | 40/75 | 3.3/4.1 | 3.3/NA | 3.2/NA | 2.9/NA | 2.9/11.4 | | | | | |
| 7 | 75 mg/60/100 cc | 25/60 | 3.2/3.9 | 3.2/NA | 3.3/NA | 3.3/4.5 | 3.5/5.3 | 3.2/4.9 | 4.6/NA | 4.1/6.1 | 3.6/NA | 4.6/NA |
| 7 | 75 mg/60/100 cc | 40/75 | 3.2/3.9 | 3.2/NA | 3.1/NA | 3.2/8.0 | 3.7/13.5[1] | | | | | |
| 7 | 75 mg/300/400 cc | 25/60 | 3.2/3.9 | 3.4/NA | 3.4/NA | 3.4/4.8 | 3.7/5.5 | 3.4/5.2 | 4.9/NA | 4.2/6.4 | 3.8/NA | 4.7/NA |
| 7 | 75 mg/300/400 cc | 40/75 | 3.2/3.9 | 3.3/NA | 3.3/NA | 3.5/9.1 | 3.9/13.6[1] | | | | | |
| 7 | 75 mg/60/bulk | 25/60 | 3.2/3.9 | 3.3/NA | 3.3/NA | 3.2/NA | 3.5/5.2 | 2.9/NA | 4.0/5.5 | | | |
| 7 | 75 mg/60/bulk | 40/75 | 3.2/3.9 | 3.2/NA | 3.2/NA | 2.9/NA | 2.8/10.3 | | | | | |
| 8 | 25 mg/60/50 cc | 25/60 | 3.1/3.9 | 3.1/NA | 3.1/NA | 3.0/4.1 | 3.4/4.9 | 3.1/4.9 | 3.7/NA | 3.4/5.3 | 3.4/NA | 4.3/NA |
| 8 | 25 mg/60/50 cc | 40/75 | 3.1/3.9 | 3.0/NA | 2.9/NA | 2.7/7.4 | 3.4/13.4[1] | | | | | |
| 8 | 25 mg/420/250 cc | 25/60 | 3.1/3.9 | 3.2/NA | 3.3/NA | 3.3/4.6 | 3.6/5.3 | 3.4/5.0 | 4.1/NA | 4.5/6.8 | 3.8/NA | 4.6/NA |
| 8 | 25 mg/420/250 cc | 40/75 | 3.1/3.9 | 3.3/NA | 3.3/NA | 3.2/9.1 | 4.0/16.2[1] | | | | | |
| 8 | 25 mg/60/bulk | 25/60 | 3.1/3.9 | 3.3/NA | 3.2/NA | 3.1/NA | 3.3/4.7 | 3.0/NA | 3.4/4.9 | | | |
| 8 | 25 mg/60/bulk | 40/75 | 3.1/3.9 | 3.2/NA | 3.0/NA | 2.8/NA | 2.7/10.6 | | | | | |
| 9 | 25 mg/60/50 cc | 25/60 | 3.6/4.2 | 3.5/NA | 2.9/NA | 3.2/4.0 | 3.4/4.4 | 3.3/4.6 | 3.4/5.0 | | | |
| 9 | 25 mg/60/50 cc | 40/75 | 3.6/4.2 | 3.4/NA | 2.7/NA | 3.0/6.8 | 3.4/11.4 | | | | | |
| 9 | 25 mg/420/250 cc | 25/60 | 3.6/4.2 | 3.5/NA | 3.0/NA | 3.4/4.3 | 3.4/4.4 | 3.5/5.0 | 3.8/5.8 | | | |
| 9 | 25 mg/420/250 cc | 40/75 | 3.6/4.2 | 3.5/NA | 3.0/NA | 3.5/7.9 | 3.8/12.9 | | | | | |
| 9 | 25 mg/60/bulk | 25/40 | 3.6/4.2 | 3.5/NA | 3.0/NA | 3.3/NA | 3.3/4.2 | 3.1/4.2 | 3.1/4.6 | | | |
| 9 | 25 mg/60/bulk | 40/75 | 3.6/4.2 | 3.3/NA | 2.8/NA | 3.0/NA | 2.8/9.1 | | | | | |
| 10 | 25 mg/60/50 cc | 25/60 | 3.4/4.0 | NA | NA | 3.1/3.9 | 3.1/4.1 | 2.9/4.2 | 3.1/4.7 | | | |
| 10 | 25 mg/60/50 cc | 40/75 | 3.4/4.0 | NA | NA | 2.7/7.0 | 3.2/11.9 | | | | | |

[1]Samples pulled at 6 months but held at room temperature until new reference standard was qualified (at 8 months)

All of the foregoing CBGB samples met the acid resistance criteria (Not more than 10% (Q) of the label claim of cysteamine is dissolved after 2 hours in 0.1N HCl) and dissolution criteria (Not less than 70% (Q) of the label claim of cysteamine is dissolved after 30 minutes in 0.2M sodium phosphate buffer, pH 6.8)

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A pharmaceutical dosage form, comprising delayed-release cysteamine beads, the beads comprising:
   (i) a core particle comprising cysteamine or a pharmaceutically acceptable salt thereof and a binder, and
   (ii) an enteric membrane surrounding the core particle,
wherein the beads have a distribution of particle sizes in a range of about 0.7 mm to about 2.8 mm;
wherein the enteric membrane begins to dissolve within a pH range of about 4.5 to about 6.5;
wherein the enteric membrane is present in an amount in a range of about 25% to about 35% by weight, based on the weight of the core particles; and
wherein the pharmaceutical dosage form, upon administration in a capsule to fasted healthy normal subjects at 600 mg free cysteamine base, provides:
   (a) a mean Cmax upon oral dosing in a range of 2.3±0.6 mg/L or in a range of 80% to 125% thereof; and
   (b) a mean AUC (0-inf_D) upon oral dosing in a range of 0.84±0.19 min*mg/L/mg or in a range of 80% to 125% thereof.

2. The pharmaceutical composition of claim 1, wherein the particle sizes of the beads are in a range of about 0.7 mm to about 2.5 mm.

3. The pharmaceutical dosage form of claim 1, wherein the distribution of bead sizes is characterized by at least 80% by weight of the beads having a particle size in a range of about 850 μm to about 1180 μm.

4. The pharmaceutical composition of claim 1, wherein 5% or less of the beads by weight are retained on a #12 mesh (1.68 mm) screen and 10% or less by weight pass through a #20 mesh (0.84 mm) screen.

5. The pharmaceutical composition of claim 1, wherein the distribution of bead sizes is characterized by less than 5% by weight of the beads being retained on a 1400 μm sieve.

6. The pharmaceutical dosage form of claim 1, wherein the distribution of bead sizes is characterized by less than 30% by weight of the beads being retained on a 1180 μm sieve.

7. The pharmaceutical dosage form of claim 1, wherein the distribution of bead sizes is characterized by less than 70% by weight of the beads being retained on a 1000 μm sieve.

8. The pharmaceutical dosage form of claim 1, wherein the distribution of bead sizes is characterized by less than 20% by weight of the beads being retained on a 850 μm sieve.

9. The pharmaceutical dosage form of claim 1, wherein the distribution of bead sizes is characterized by at least 15% by weight of the beads being retained on a 1180 μm sieve.

10. The pharmaceutical dosage form of claim 1, wherein the distribution of bead sizes is characterized by at least 50% by weight of the beads being retained on a 1000 μm sieve.

11. The pharmaceutical dosage form of claim 1, wherein the distribution of bead sizes is characterized by at least 10% by weight of the beads being retained on a 850 μm sieve.

12. The pharmaceutical dosage form of claim 1, wherein the distribution of bead sizes is characterized by a median particle size in a range of about 850 μm to about 1180 μm.

13. The pharmaceutical dosage form of claim 1, wherein the bead core particle further comprises a filler.

14. The pharmaceutical dosage form of claim 1, wherein the cysteamine (as free base) is present in the bead core particle in an amount of at least 10 wt. %.

15. The pharmaceutical dosage form of claim 1, wherein the cysteamine or pharmaceutically acceptable salt thereof is a pharmaceutically acceptable salt of cysteamine.

16. The pharmaceutical dosage form of claim 1, wherein 5% or less of the bead core particles by weight are retained on a #12 mesh (1.68 mm) screen and 10% or less by weight pass through a #20 mesh (0.84 mm) screen.

17. The pharmaceutical dosage form of claim 1, wherein the enteric-coated beads are characterized by acid resistance such that not more than 10% of the cysteamine in the beads is dissolved after a period of two hours in a 0.1N HCl solution.

18. The pharmaceutical dosage form of claim 1, wherein the enteric-coated beads are characterized by dissolution such that 80% of the cysteamine or pharmaceutically acceptable salt thereof is released within 20 minutes in a solution buffered at pH 6.8.

19. The pharmaceutical dosage form of claim 1, further comprising a capsule shell enclosing the plurality of beads.

20. The pharmaceutical dosage form of claim 1, wherein the beads provide a mean Cmax and mean AUC (0-inf_D) upon oral dosing, fasted, when administered inside a capsule shell that are bioequivalent to the mean Cmax and mean AUC (0-inf_D) upon oral dosing, fasted, when administered without a capsule shell.

21. The pharmaceutical dosage form of claim 1, wherein the enteric membrane comprises an enteric material that begins to dissolve at pH of about 5.5 in an aqueous solution.

22. The pharmaceutical dosage form of claim 1, wherein the pharmaceutical dosage form, upon administration in a capsule to fasted healthy normal subjects at 600 mg free cysteamine base, provides:
   (a) a mean Cmax upon oral dosing in a range of 2.3±0.6 mg/L; and (b) a mean AUC (0-inf_D) upon oral dosing in a range of 0.84±0.19 min*mg/L/mg.

23. The pharmaceutical dosage form of claim 1, wherein the pharmaceutical dosage form, upon administration in a capsule to fasted healthy normal subjects at 600 mg free cysteamine base, provides:
  (a) a mean Cmax upon oral dosing of 2.3 mg/L or in a range of 80% to 125% thereof; and
  (b) a mean AUC (0-inf_D) upon oral dosing of 0.84 min*mg/L/mg or in a range of 80% to 125% thereof.

* * * * *